(12) United States Patent
Gueziec et al.

(10) Patent No.: US 6,301,495 B1
(45) Date of Patent: Oct. 9, 2001

(54) SYSTEM AND METHOD FOR INTRA-OPERATIVE, IMAGE-BASED, INTERACTIVE VERIFICATION OF A PRE-OPERATIVE SURGICAL PLAN

(75) Inventors: Andre Gueziec, Mamaroneck; Alan David Kalvin, Irvington, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/299,643

(22) Filed: Apr. 27, 1999

(51) Int. Cl.[7] .................................................... A61B 5/05
(52) U.S. Cl. ................................................... 600/407
(58) Field of Search .................................. 600/407, 410, 600/411, 414, 416, 417, 425, 426, 427; 382/128, 132

(56) References Cited

U.S. PATENT DOCUMENTS 5,568,384 * 10/1996 Robb et al. ........................ 382/132

5,951,475 * 9/1999 Gueziec et al. ...................... 600/425

* cited by examiner

*Primary Examiner*—George Manuel
(74) *Attorney, Agent, or Firm*—Louis J. Percello, Esq.; McGinn & Gibb, PLLC (57) ABSTRACT

A system and method for intra-operatively providing a surgeon with visual evaluations of possible surgical outcomes ahead of time, and generating simulated data, includes a medical imaging camera, a registration device for registering data to a physical space, and to the medical imaging camera, and a fusion mechanism for fusing the data and the images to generate simulated data. The simulated data (e.g., such as augmented X-ray images) is natural and easy for a surgeon to interpret. In an exemplary implementation, the system preferably includes a data processor which receives a three-dimensional surgical plan or three-dimensional plan of therapy delivery, one or a plurality of two-dimensional intra-operative images, a three-dimensional model of pre-operative data, registration data, and image calibration data. The data processor produces one or a plurality of simulated post-operative images, by integrating a projection of a three-dimensional model of pre-operative data onto one or a plurality of two-dimensional intra-operative images.

46 Claims, 8 Drawing Sheets

SYSTEM AND METHOD FOR INTRA-OPERATIVE, IMAGE-BASED, INTERACTIVE VERIFICATION OF A PRE-OPERATIVE SURGICAL PLAN

BACKGROUND OF THE INVENTION

1. Field of the Invention

The present invention generally relates to robotics and medical imaging techniques and, more particularly to robotically-assisted surgical systems and other devices incorporating methods for registering image data (both pre-operative and intra-operative) to physical space and for providing feedback, and in particular visual feedback, to the clinician.

2. Description of the Related Art

Computers are increasingly used to plan complex surgeries by analyzing pre-operative Computed Tomography (CT) or Magnetic Resonance Imaging (MRI) scans of a patient.

To execute the surgical plan, it is important to accurately align or register the three-dimensional pre-operative and intra-operative data to an actual location of the patient's anatomical features of interest during surgery.

One conventional technique for performing this type of registration is to attach a stereo-tactic frame or fiducial markers to the patient, and to precisely locate the frame or markers prior to and during surgery.

For example, in the case of a surgery involving a patient's femur, a conventional registration protocol includes implanting three metallic markers or pins in the patient's femur (e.g., one proximally in the trochanter and two distally in the condyles, near the knee). However, the insertion of the pins requires minor surgery. A CT-scan image of the patient is subsequently acquired. By analyzing the CT data, the surgeon decides upon the size and location of the implant that best fits the patient's anatomy. During surgery, the metallic pins are exposed at the hip and knee. The patient's leg is attached to a surgical robot device that then must locate the exposed pins. A registration, or coordinate transformation from CT space to robot space, is computed using the locations of the three pins as a Cartesian frame. The accuracy of this registration has been measured to be better than one millimeter. This conventional registration protocol is described in U.S. Pat. No. 5,299,288 entitled "IMAGE-DIRECTED ROBOTIC SYSTEM FOR PRECISE ROBOTIC SURGERY INCLUDING REDUNDANT CONSISTENCY CHECKING" by Glassman et al., and incorporated herein by reference.

However, using such pins as markers is not always desirable, as they may cause significant patient discomfort, and the required surgical procedure to insert and subsequently remove the pins is inconvenient and costly to the patient.

An alternative registration technique is to perform anatomy-based registration that uses anatomical features of the patient (e.g., generally bone features), as markers for registration. Conventional methods for performing anatomy-based registration are described in "Registration of Head CT Images to Physical Space Using a Weighted Combination of Points and Surfaces" by Herring et al., in *IEEE Transactions on Medical Imaging*, Vol. 17, No 5, pages 753–761, 1998 and in U.S. patent application Ser. No. 08/936,935 entitled "METHODS AND APPARATUS FOR REGISTERING CT-SCAN DATA TO MULTIPLE FLUOROSCOPIC IMAGES", filed on Sep. 27, 1997 by A Gueziec et al., each of which is herein incorporated by reference in its entirety.

Once the registration has been performed, it is important to provide the clinician with means to assess the registration, allowing him or her to validate, reject or improve the registration (and the surgical plan). A system and method for advising a surgeon is described in U.S. Pat. No. 5,445,166, entitled "SYSTEM FOR ADVISING A SURGEON", by Taylor, which is herein incorporated by reference in its entirety. Taylor describes a system for guiding the motions of a robot, or of a positioning device controlled by motors, and teaches how audio feedback and force feedback can be provided to a surgeon. Taylor also describes a visual adviser allowing comparison of the surgical plan with its execution. The system taught by Taylor optionally uses a camera at the end of a surgical instrument that sends an image to the graphics adapter, optionally mixed with graphics output of the computer.

A conventional technique for simulating a post-operative X-ray image is described in "An Overview of Computer-Integrated Surgery at the IBM T. J. Watson Research Center" by Taylor et al., in *IBM Journal of Research*, 1996, which is herein incorporated by reference in its entirety.

Thus, conventional techniques are useful for registering three-dimensional pre-operative and intra-operative data to an actual location of anatomical features of interest during surgery, and to provide advice to the surgeon. However, none of the conventional techniques teaches how to simulate a post-operative condition depending upon the registration of image data to physical space, by fusing intra-operative images with registered pre-operative data, and generating new images.

In Taylor et al., the simulated post-operative X-ray image is generated using only pre-operative CT (Computed Tomography) data. Herring et al. do not teach how to evaluate the registration accuracy intra-operatively.

Although Glassman et al.'s and Taylor's systems compare a surgical plan and its execution, neither Glassman et al. nor Taylor teaches how to simulate the outcome of a surgical plan prior to the actual execution of the plan. With Taylor's system, a surgeon can take corrective measures to minimize the effects of a wrongful execution of the plan, but cannot make a decision before any execution of the plan and therefore cannot prevent all errors before they occur.

Further, the information produced by Taylor's system for advising a surgeon is not represented in the form of conventional medical media (e.g., such as X-ray images) and require an extra burden on the surgeon in order to interpret and evaluate this information.

Thus, it is believed that conventional techniques do not exist (or at the very least are inadequate) for (a) providing the surgeon with post-operative evaluations prior to surgery, that are obtained by merging intra-operative image data and pre-operative data, and (b) presenting such evaluations in a standard clinical fashion (e.g., such as augmented X-ray images) that is natural for a surgeon to interpret.

Other problems of the conventional systems and methods include the limited availability of 2-D/3-D registration methods in conventional art systems for advising a surgeon and the 2-D/3-D registration postdates.

SUMMARY OF THE INVENTION

In view of the foregoing and other problems of the conventional methods and structures, an object of the present invention is to provide a method and structure for intra-operatively providing the surgeon with visual evaluations of possible surgical outcomes ahead of time, the evaluations being obtained by merging intra-operative image data and pre-operative data, and presented in a standard clinical fashion (e.g., such as augmented X-ray images) that is natural and easy for a surgeon to interpret.

Another object of the present invention is to provide a system and method for comparing several registration methods of pre-operative data to the physical space of the operating room.

Yet another object of the present invention is to provide a system and method for assisting the surgeon in improving an inaccurate registration of a pre-operative surgical plan to the physical space.

Still another object of the present invention is to provide an improved robotically assisted surgical system that also provides visual post-operative evaluations.

A further object of the present invention is to provide an improved robotically-assisted surgical system that includes a system for assisting the surgeon in improving a registration.

Another object of this invention is to provide an improved robotically assisted surgical system that includes a system for preventing surgical errors caused by internal failure of the robot's calibration system.

The present invention includes a system to intra-operatively provide the surgeon with visual evaluations of possible surgical outcomes ahead of time, the evaluations being obtained by merging intra-operative image data and pre-operative data, and being presented in a standard clinical fashion (e.g., such as augmented X-ray images) that is natural and easy for a surgeon to interpret.

The inventive system preferably includes a data processor. The data processor takes as inputs a three-dimensional surgical plan or three-dimensional plan of therapy delivery, one or a plurality of two-dimensional intra-operative images, a three-dimensional model of pre-operative data, registration data, and image calibration data.

The data processor produces one or a plurality of simulated post-operative images, by integrating a projection of a three-dimensional model of pre-operative data onto one or a plurality of two-dimensional intra-operative images.

The data processor optionally receives an input from a surgeon or a clinician. The input preferably includes a set of constraints on the surgical plan or plan of therapy delivery. The data processor preferably optimizes the surgical plan or plan of therapy delivery using the constraints.

In a first aspect of the present invention, a system (and method) for generating simulated data, includes a medical imaging camera for generating images, a registration device for registering data to a physical space, and to the medical imaging camera, and a fusion (integration) mechanism for fusing (integrating) the data and the images to generate simulated data.

In another aspect of the invention, a signal-bearing medium is provided for storing a program for performing the method of the invention. Other aspects of the invention are also set forth below.

With the invention, the surgeon is provided with intra-operative visual evaluations of possible surgical outcomes in advance, with the evaluations being obtained by merging intra-operative image data and pre-operative data. Such evaluations are presented in a standard clinical fashion that is natural and easy for a surgeon to interpret. Further, the inventive system compares several registration methods of pre-operative data to the physical space of the operating room.

Moreover, the invention assists the surgeon in improving an inaccurate registration of a pre-operative surgical plan to the physical space. Additionally, the system can be robotically-assisted and can provide visual post-operative evaluations.

Finally, in the robotically-assisted implementation of the inventive system, surgical errors, caused by internal failure of the robot's calibration system, can be prevented.

BRIEF DESCRIPTION OF THE DRAWINGS

The foregoing and other purposes, aspects and advantages will be better understood from the following detailed description of preferred embodiments of the invention with reference to the drawings, in which.

DETAILED DESCRIPTION OF PREFERRED EMBODIMENTS OF THE INVENTION

Referring now to the drawings, and more particularly to FIGS. 1–12, there are shown preferred embodiments of the method and structures according to the present invention.

Generally, the present invention resides in a system and method to intra-operatively provide the surgeon with visual evaluations of possible surgical outcomes ahead of time, the evaluations being obtained by merging intra-operative image data and pre-operative data, and being presented in a standard clinical fashion (such as augmented X-ray images) that is natural and easy for a surgeon to interpret.

A novel aspect of the present invention is to allow intra-operative manipulation of a model (e.g., such as a CAD model of an implant) as opposed to a real object (e.g., such as a cutter of a surgical robot as in Taylor's system).

Figure 1:
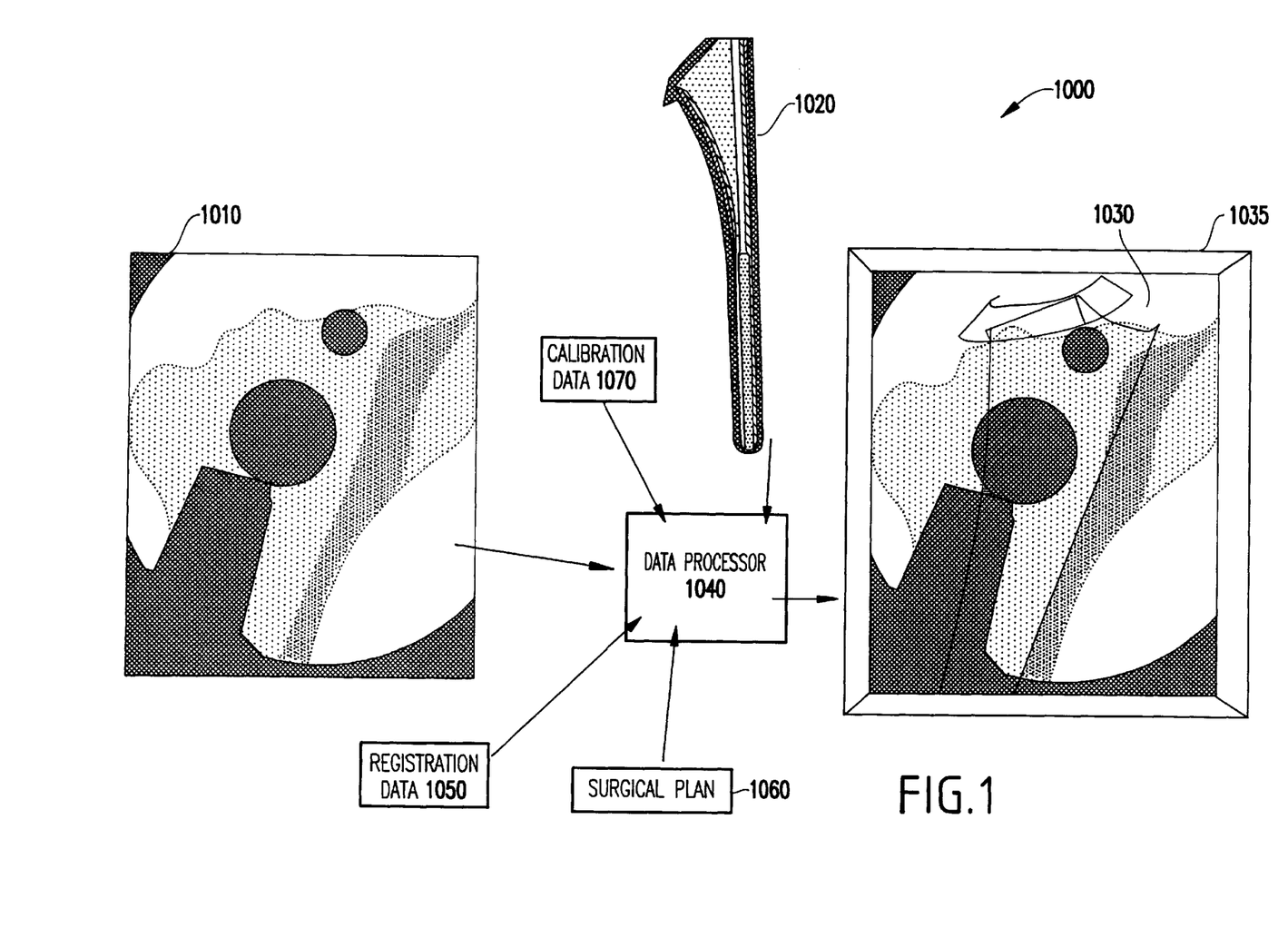
FIG. 1 is a block diagram of a preferred embodiment of a system according to the present invention.

Referring to FIG. 1, a system 1000 according to the present invention uses a two-dimensional intra-operative image 1010 (e.g., a two-dimensional X-ray or other type of image) and a three-dimensional shape of a prosthetic implant 1020, and comprises a data processor 1040. The pre-operative image (e.g., of the shape of the implant with respect to anatomical features) may be obtained by an X-ray, computed tomography (CT) scanner, whereas the intra-operative image(s) may be obtained by a two-dimensional (2D) X-ray camera.

The data processor 1040 receives the image 1010 and the shape 1020, as well as registration data 1050 and a surgical plan 1060. The registration data registers the shape 1020 with the camera used for acquiring the image 1010. An example of registration process producing registration data 1050 is provided in the above-mentioned U.S. patent application Ser. No. 08/936,935, previously incorporated by reference.

A typical example of the surgical plan 1060 is a planned type, orientation and position of an implant relative to anatomical structures in a pre-operative CT scan. Another example of the surgical plan 1060 is the planned type, orientation and position of an implant relative to co-registered intra-operative X-ray images of anatomical structures.

Image calibration data 1070 is also input to the data processor. The data processor 1040 produces a simulated post-operative image 1030. Image 1030 may be presented visually to the surgeon on a display 1035. That is, the post-operative simulation (e.g., data which preferably includes an image such as a 2-dimensional image) may be displayed on any of a cathode ray tube (CRT), liquid crystal display (LCD), or the like.

Figure 2:
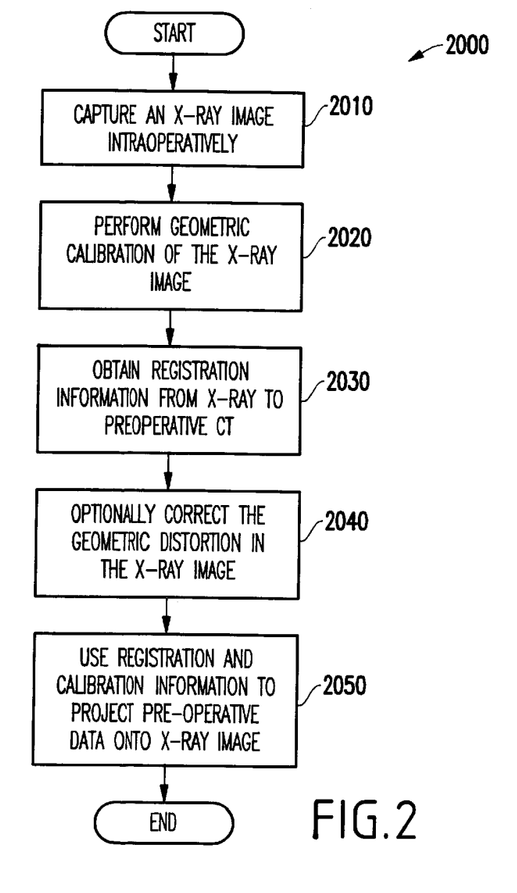
FIG. 2 is a flow chart showing an overview of a process to generate a post-operative simulation.

Referring now to FIG. 2, the operation of the present invention will be described hereinbelow. FIG. 2 is a flow chart illustrating how a post-operative simulation can be generated using the present invention.

In Step 2010, an image (e.g., an X-ray image or other intra-operative image 1010 as shown in FIG. 1) is captured intra-operatively. Conventional methods for capturing an X-ray image include using a frame grabber connected to the video output of a conventional fluoroscope. Fluoroscopes are manufactured by many medical imaging equipment manufacturers. An example of a fluoroscope is the Ziehm Exposcop Plus® System (Exposcop Plus is a trademark of the Ziehm Corporation). Another method for capturing an X-ray image intra-operatively is to use an X-ray flat panel detector. An example of an X-ray flat panel detector is the FlashScan 30®. FlashScan 30 is a trademark of the DPIX Corporation.

Then in Step 2020, a geometric calibration of the X-ray image is performed. Geometric calibration is preferably performed using the teachings of the above-mentioned U.S. patent application Ser. No. 08/936,935.

In Step 2030, X-ray and pre-operative CT data are registered (e.g., this data represents the registration data 1050 of FIG. 1). A preferred method for registering X-ray and pre-operative CT data is described in the abovementioned U.S. patent application Ser. No. 08/936,935.

Then, in Step 2040, the geometric distortion of the X-ray image is corrected. Further understanding of Step 2040 can be achieved with reference to FIGS. 5–7 described below.

In Step 2050, the registration and calibration are used to project pre-operative data such as a three-dimensional shape of an implant (e.g., shape 1020 in FIG. 1) onto the X-ray image. The result is the simulated post-operative image 1030 in FIG. 1.

Figure 3:
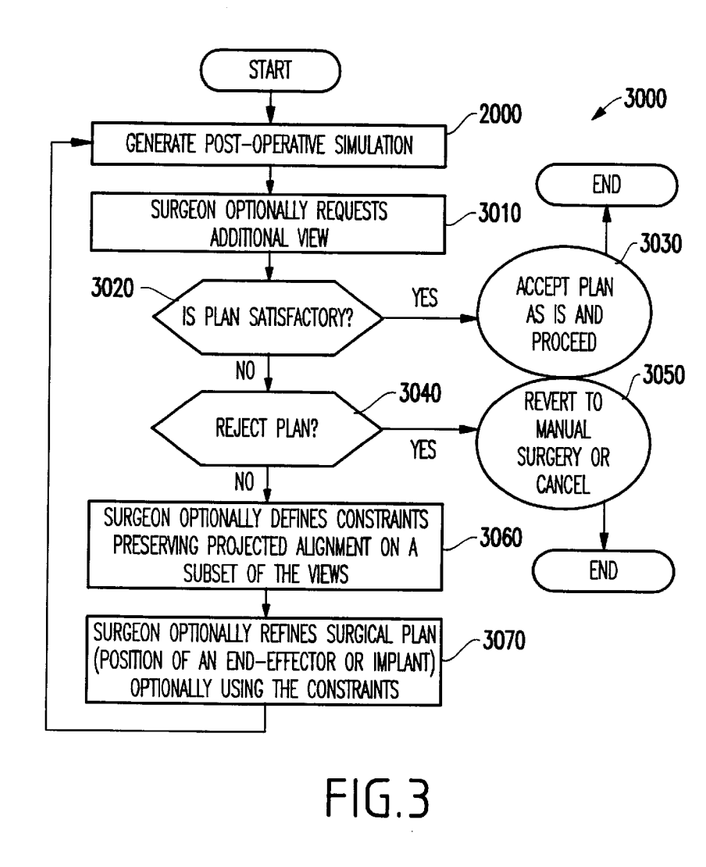
FIG. 3 is a flow chart showing an overview of a process for validating, rejecting or improving a surgical plan using post-operative simulations.

FIG. 3 is a flow chart showing an overview of a process for validating, rejecting or improving a surgical plan using post-operative simulations.

In Step 2000, a post-operative simulation (as described above in FIG. 2) is generated using the present invention. After reviewing this simulation on the display or the like, the surgeon may optionally request one or more additional 2D X-ray views to assist in evaluating the simulation, as shown in Step 3010.

In Step 3020, the surgical plan is evaluated as follows: (1) if the surgeon evaluates it as being satisfactory, the plan is accepted as is, and the surgery proceeds (Step 3030); (2) if the plan is considered unsatisfactory, the plan is either (a) rejected (Step 3040), and, as shown in Step 3050, the surgeon reverts to manual surgery or the surgical procedure is canceled, or (b) the plan is modified, as shown in Steps 3060–3070.

In Step 3060, the surgeon has the option to specify additional three-dimensional constraints in a manner that preserve existing three-dimensional constraints. That is, the surgeon may define constraints that preserve a projected alignment on a subset of the total number of views. For example, the surgeon can indicate "prohibited regions" on one or more of the two-dimension images, where such regions are "off limits" to the prosthesis being implanted.

Typical "off-limit" regions are those close to critical arteries, nerves, or regions where the bone is very thin and fragile. Each of such two-dimensional "prohibited regions" corresponds to a three-dimensional "prohibited volume" that is defined by the 2-D region and the projection geometry. It is noted that these existing three-dimensional constraints are a subset of the constraints that are represented in the existing two-dimensional X-ray views.

In Step 3070, the surgeon optionally refines the surgical plan (e.g., adjusting the position of an end-effector or prosthetic implant, etc.) based on the existing three-dimensional constraints and those new constraints produced in Step 3060. A typical example of the refinement process occurs if the surgeon sees that the planned position for implanting a prosthesis is unsatisfactory because the implant will impinge on a region of thin bone, thereby increasing the chance of subsequent bone-fracture. The surgical procedure is therefore refined by calculating a modified position for the implant relative to the patient.

Then, the process loops to step 2000, and a new post-operative simulation is now generated. The sequence of steps 2000, 3010, 3020, 3040, 3060, 3070 is repeated until the resulting surgical plan is accepted (Step 3030) or rejected (Step 3050).

Figure 4:
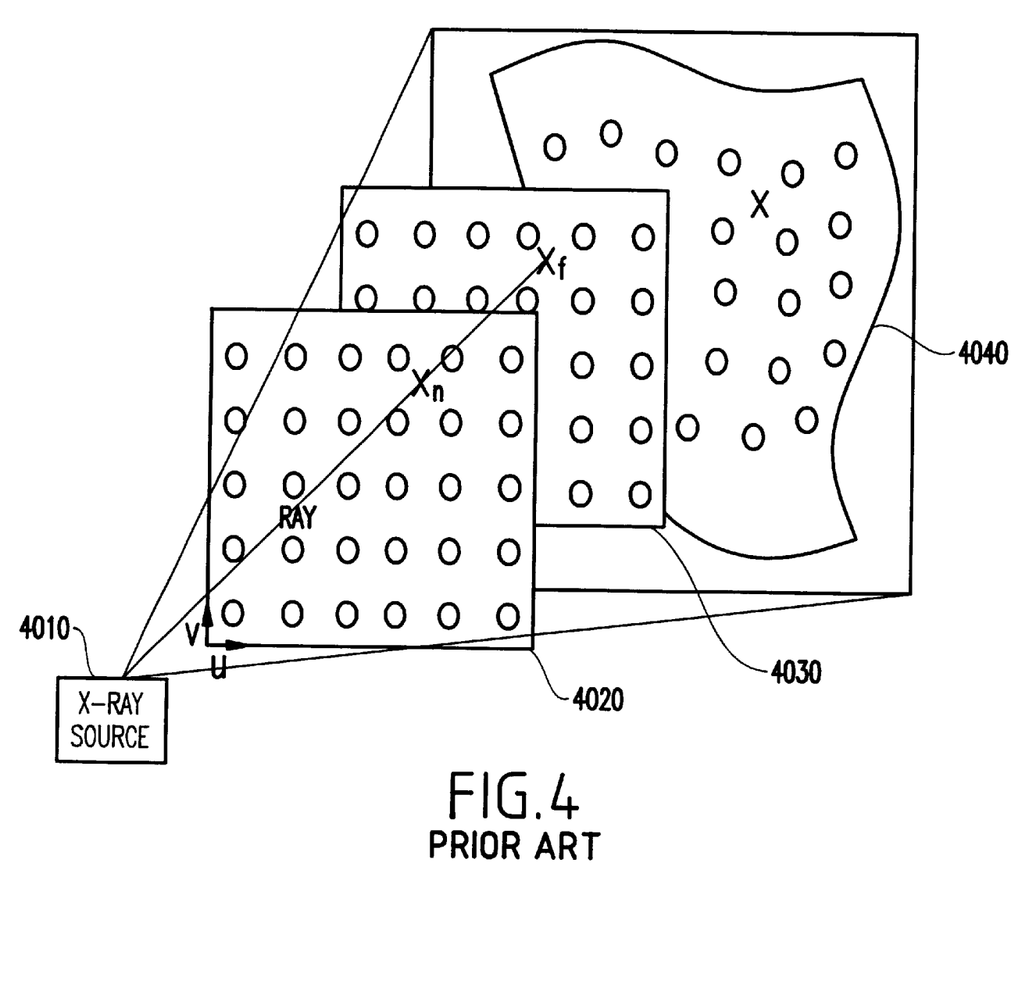
FIG. 4 is a diagram illustrating a preferred method for calibrating intra-operative images with respect to a coordinate system of relevance.

Referring now to FIG. 4, the geometric calibration of an X-ray image of Step 2020 will be further described below.

As shown in FIG. 4, both a near grid 4020 of markers and a far grid 4030 of markers are positioned in front of an X-ray source 4010. Distorted grid points (e.g., distorted because of the physical process of x-ray image capture using an image intensifier and because of other potential optical distortions) are observed on one or a plurality of captured distorted images 4040. Any image pixel x can be associated to two locations $x_n$ (near grid) and $x_f$ (far grid) on the grids, specifying a ray in three dimensions.

Figure 5:
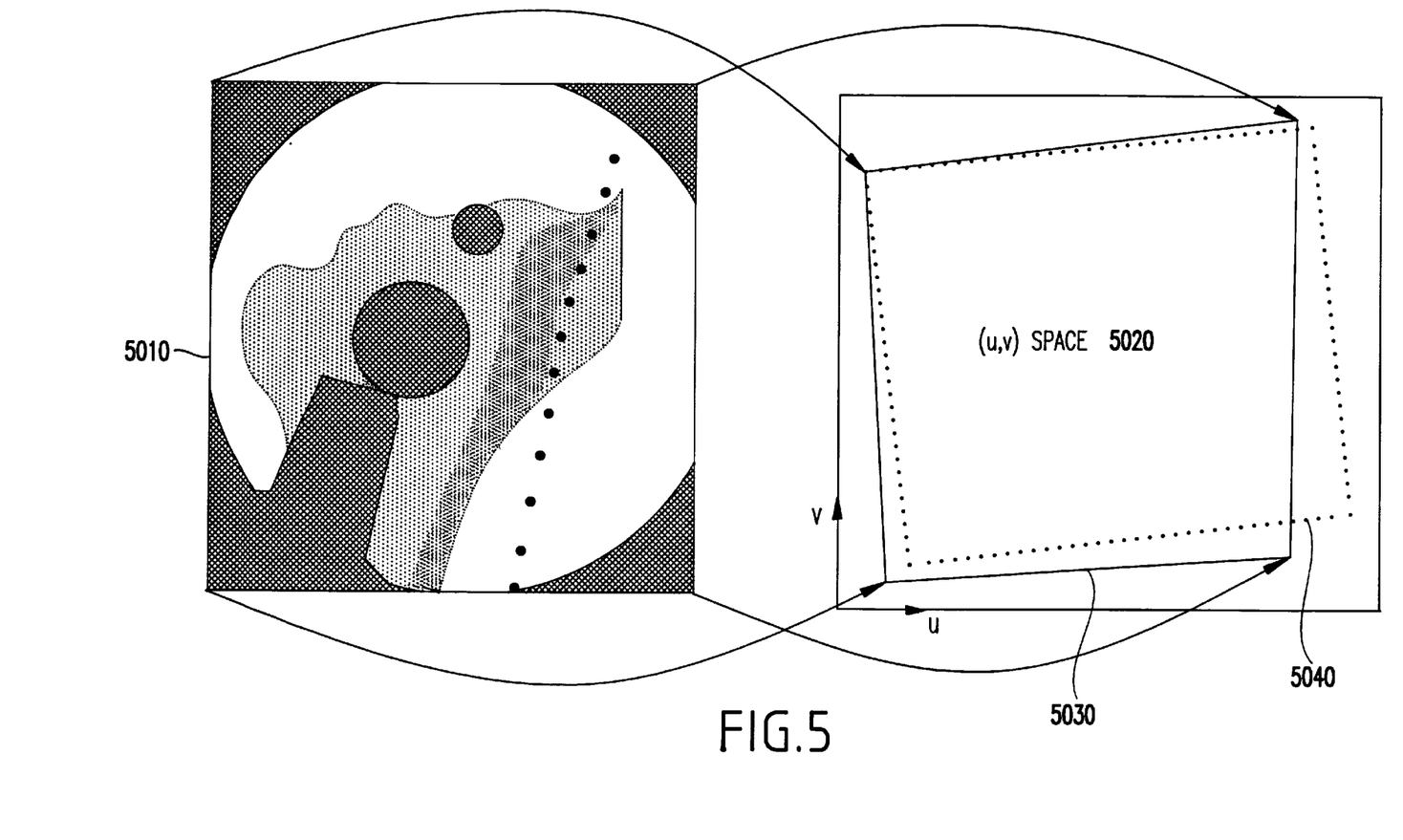
FIG. 5 is a diagram illustrating a preferred method for generating a reformatted and optionally undistorted image from an intra-operative image.
Figures 6, 7:
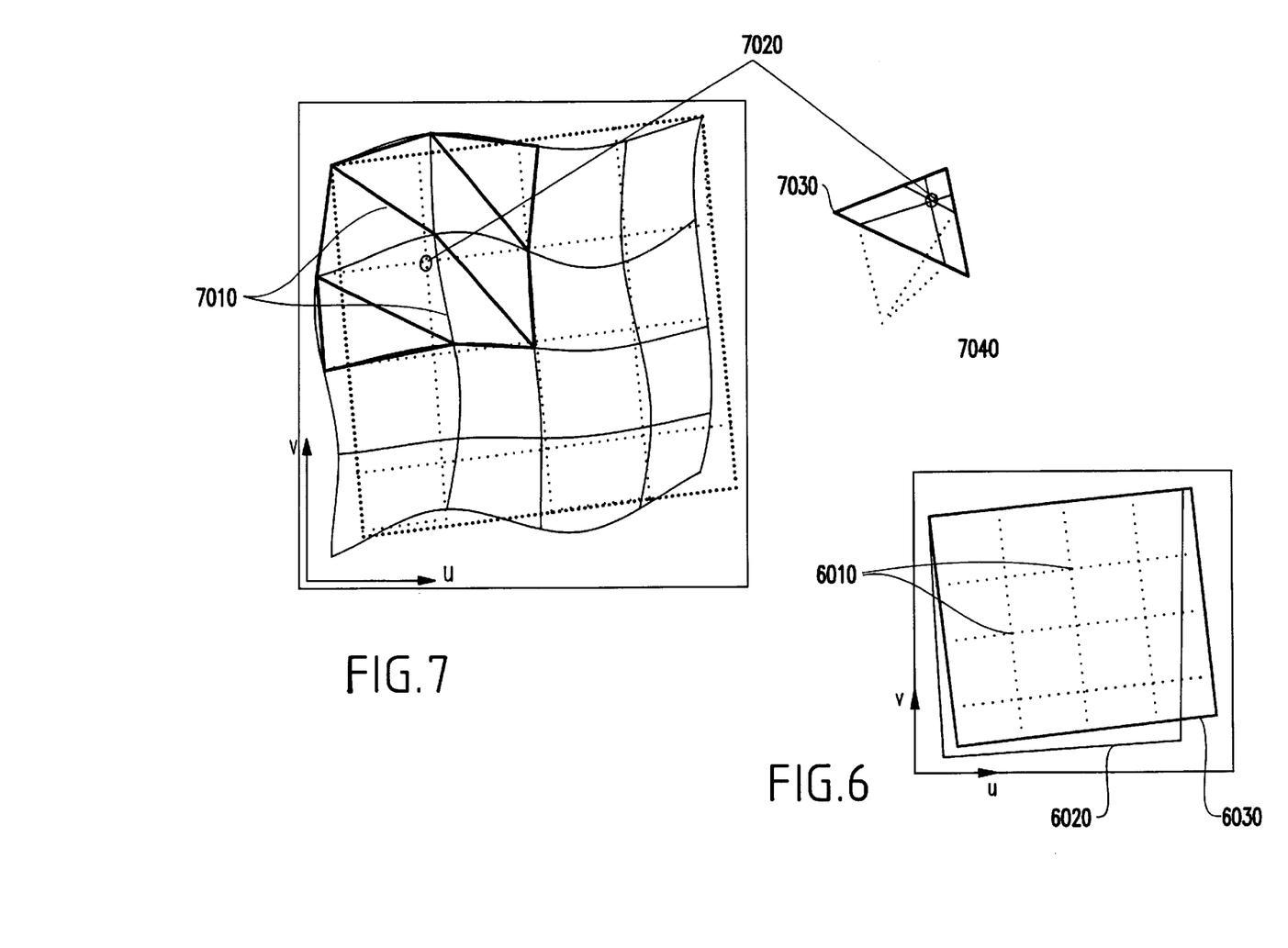
FIG. 6 is a diagram illustrating a method for determining a new image resolution and new pixel locations.
FIG. 7 is a diagram illustrating a method for determining image gray-scale values corresponding to new pixel locations.

Referring now to FIGS. 5–7, the correction of geometric distortion in X-ray images of Step 2040 will be described in detail.

As shown in FIG. 5, each pixel of a distorted X-ray image 5010 is mapped to (u, v)-space 5020 (or any suitable coordinate system) of any one of the near grid 4020 of markers or the far grid 4030 of markers.

The four corner pixels of the image 5010 are preferably mapped to (u, v)-space 5020, and a quadrilateron 5030 of transformed corner pixels is obtained.

Then, a rectangular area 5040 bounding the distortion-corrected image is determined. A preferred method for determining the rectangular area 5040 is to use the first and last transformed pixels of the first pixel row of image 5010 to define a first side of the rectangular area 5040 and to determine a second side, orthogonal to the first side, whose length is equal to the distance between the first and last transformed pixels of the first pixel column of image 5010.

Referring to FIG. 6, new pixel locations 6010 are preferably determined by dividing a rectangular boundary 6030 of a distortion-corrected image determined with the rectangular area 5040 in substantially equally sized square pixels, the rectangular boundary 6030 approximating an area 6020 of a transformed image.

Referring to FIG. 7, a triangular mesh 7010 is defined by transforming the pixels of the distorted image and connecting the transformed pixel location with triangles.

For each new pixel 7020, a closest triangle is determined. A gray-scale value for the new pixel 7020 is preferably determined using gray-scale values of the three corners 7030 of the closest triangle, by interpolating the gray scale values of the three corners of the closest triangle using triangle barycentric coordinates 7040 of the new pixel 7020 with respect to the three corners 7030 of the closest triangle.

Figure 8:
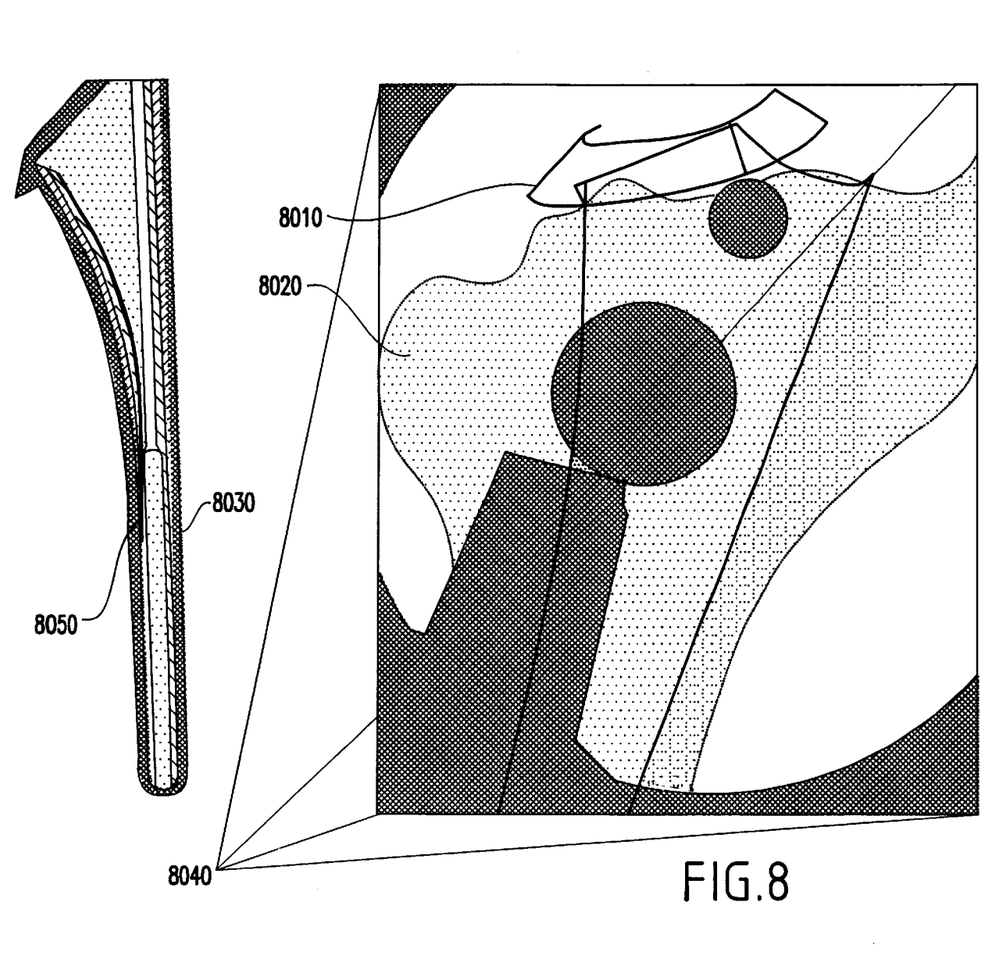
FIG. 8 is a diagram showing a simulated post-operative X-ray image.

Referring to FIG. 8, the step 2050 of using the registration and calibration to project pre-operative data, such as a three-dimensional shape of an implant, onto an X-ray image will be further described.

As shown in FIG. 8, a two-dimensional projection 8010 of a silhouette of a three-dimensional implant model 8030 is integrated in an X-ray image 8020. The process of integrating the two-dimensional projection 8010 onto the image 8020 preferably uses the following steps.

Using the calibration of the X-ray image 8020, a center of perspective 8040 is determined whose location represents an estimate of the location of an X-ray source. The center of perspective 8040 is used to compute silhouette curves 8050 on the three-dimensional implant model 8030. Silhouette curves (or apparent contours) are such that rays emanating from the center of perspective and tangent to the three-dimensional model meet the three-dimensional model on a silhouette curve. Silhouette curves are defined precisely in the above-mentioned U.S. patent application Ser. No. 08/936,935. Various techniques can be used to project silhouette curves 8050 on a two-dimensional image, such as the X-ray image 8020.

One preferred method for projecting silhouette curves is to consider in turn each new pixel 7020, determine a line in three-dimensions corresponding to that pixel by image calibration, compute the distance from the line to the silhouette curves, and assign a pixel gray-scale value depending on that distance. The distance is preferably computed using a method described in the above-mentioned U.S. patent application Ser. No. 08/936,935.

An example of assignment of pixel gray-scale values corresponding to distances is as follows.

If the distance is less than, for example, about 0.05 mm (e.g., this value can be freely selected depending on the size of the anatomical feature or area of interest, etc.), then the gray-scale value is set to 0. Otherwise, if the distance is less than about 0.1 mm, then the gray-scale value is set to 30. Otherwise, if the distance is less than 0.2 mm, then the gray-scale value is set to 60, and otherwise the gray-scale value is not modified for the purpose of projecting the silhouette curves.

It is noted that other values may be more suitable for other applications. Various techniques are known in the conventional computer graphics methods to project a three-dimensional image calibration information 1070. These conventional methods differ from the method explained previously in that individual three-dimensional polygons (or other elementary primitives) that define the shape are individually projected onto the two-dimensional image and shaded according to the orientation of normals of vertices of the three-dimensional polygon and other factors including colors potentially attached to polygon vertices. Generally, the objective is to preserve the three-dimensional appearance of the object when projecting it. Such techniques are described in standard textbooks such as "Computer Graphics: Principles and Practice" by Foley et al., Addison Wesley 1991, which is herein incorporated by reference in its entirety.

In an alternative embodiment, the silhouette curves 8050 may be projected on the two-dimensional image (e.g., by associating pixels with projected curve vertices and connecting such pixels with lines using Bresenham's line-joining algorithm, which is described in Foley et al., pages 72–73, previously incorporated by reference), forming closed two-dimensional polygonal loops.

In yet another embodiment, the closed polygonal loops may be rasterized using conventional polygon-filling methods (e.g., yielding a uniform gray level or color for the area of the two-dimensional image where the three-dimensional shape projects).

Figure 9:
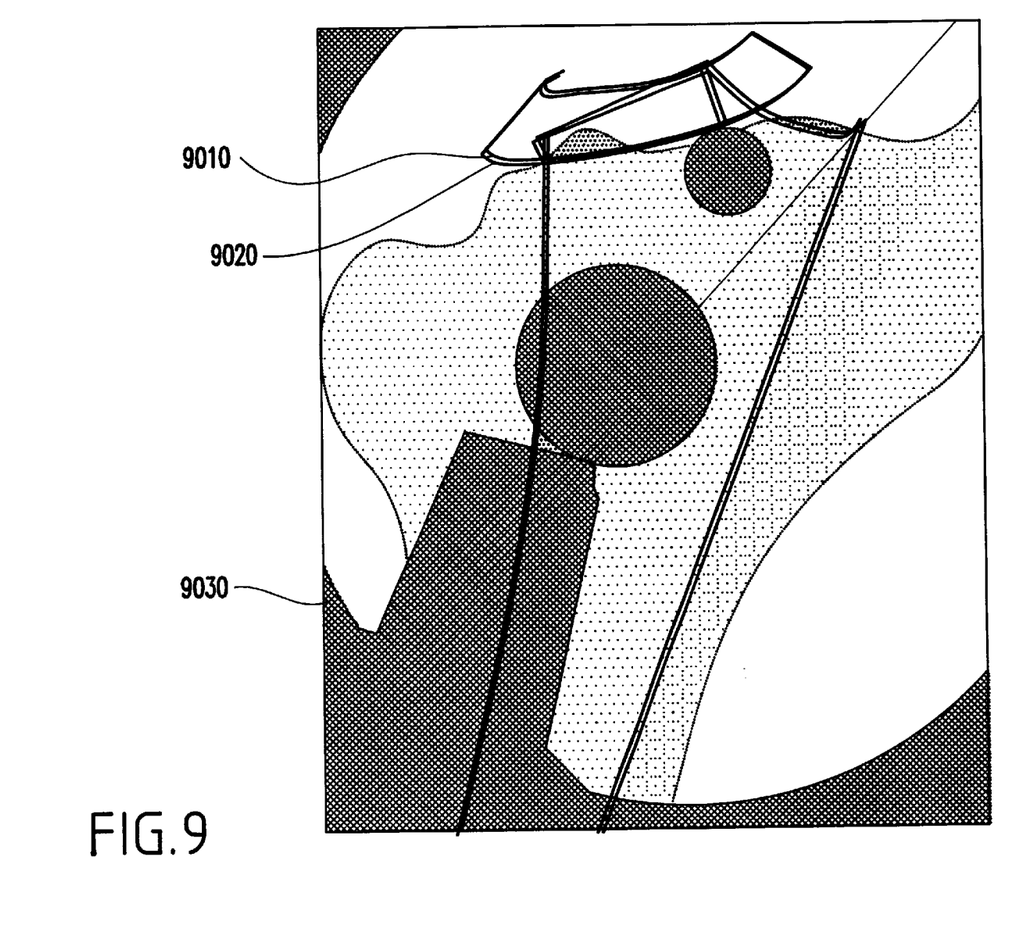
FIG. 9 is a diagram illustrating a method for comparing several registration methods.

Referring to FIG. 9, two or more registration methods (preferably used for registering pre-operative data to the physical space of the operating room) are compared by integrating a projection 9010 of an implant predicted with a first registration method (any method, e.g. by the above-mentioned "Registration of Head CT Images to Physical Space Using a Weighted Combination of Points and Surfaces" by Herring et al., in *IEEE Transactions on Medical Imaging*, Vol. 17, No 5, pages 753–761) onto an X-ray image 9030 and a second projection 9020 of an implant predicted with a second registration method. Thus, the invention provides a mechanism for comparing the efficiency of various methods.

Figure 10:
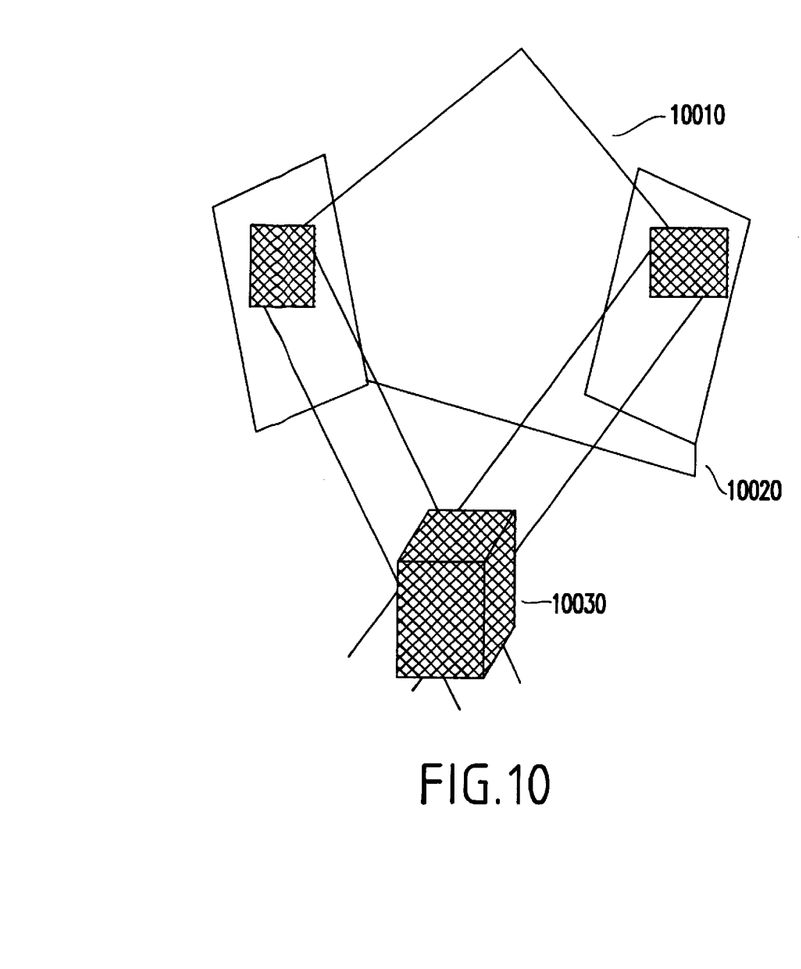
FIG. 10 is a diagram illustrating how one or several two-dimensional regions of acceptable positions can be used to define a three-dimensional region of acceptable positions.

FIG. 10 illustrates the relationship between (a) the set of three-dimensional acceptable positions 10030 of an end-effector, prosthetic implant or other object being positioned as part of the surgical plan, and (b) the two-dimensional regions of acceptable positions 10010 depicted in the two-dimensional intra-operative images 10020.

Given the set of three-dimensional acceptable positions 10030, the two-dimensional regions of acceptable positions 10010 are computed using standard conventional methods to compute two-dimensional projections of a three-dimensional object.

Figure 11:
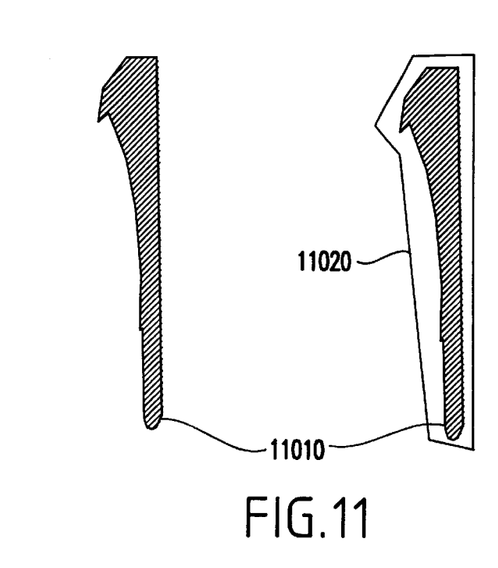
FIG. 11 is a diagram illustrating a two-dimensional region of acceptable positions.

FIG. 11 shows a technique for depicting to the surgeon the relationship between a two-dimensional projection of the end-effector, prosthetic implant or other object being positioned as part of the surgical plan 11010, and the corresponding two-dimensional region of acceptable positions 11020. The region of acceptable positions 11020 is represented as a closed two-dimensional curve.

If, in repositioning the object being positioned as part of the surgical plan, any portion of its two-dimensional projection 11010 moves outside of the two-dimensional region of acceptable positions 11020, the surgical plan is considered unacceptable. Therefore, as shown in FIG. 11, the surgeon is provided with a visual representation (e.g., on a display coupled to, for example, the data processor) to assist him in evaluating and modifying the surgical plan.

Figure 12:
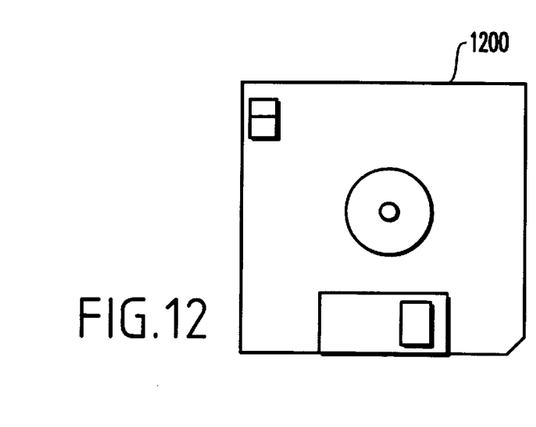
FIG. 12 illustrates a storage medium 1200 for storing steps of the program for generating a post-operative simulation.

As shown in FIG. 12, in addition to the hardware and process environment described above, a different aspect of the invention includes a computer-implemented method for generating a post-operative simulation, as described above. As an example, this method may be implemented in the particular hardware environment discussed above.

Such a method may be implemented, for example, by operating a CPU, to execute a sequence of machine-readable instructions. These instructions may reside in various types of signal-bearing media.

Thus, this aspect of the present invention is directed to a programmed product, comprising signal-bearing media tangibly embodying a program of machine-readable instructions executable by a digital data processor incorporating the CPU and hardware above, to perform a method of generating a post-operative simulation.

This signal-bearing media may include, for example, a random access memory (RAM) contained within the CPU, as represented by a fast-access storage, for example. Alternatively, the instructions may be contained in another signal-bearing media, such as a magnetic data storage diskette 1200 (FIG. 12), directly or indirectly accessible by the CPU.

Whether contained in the diskette 1200, the computer/ CPU, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog communication links and wireless. In an illustrative embodiment of the invention, the machine-readable instructions may comprise software object code, compiled from a language such as "C", etc.

While the invention has been described in terms of several preferred embodiments, those skilled in the art will recognize that the invention can be practiced with modification within the spirit and scope of the appended claims.

It is noted that the present invention can be implemented in many applications.

For example, the invention can be used in orthopedic surgery (e.g., such as total hip replacement surgery, revision total hip replacement surgery, spine surgery, etc.). In one implementation, the pre-operative images typically are three-dimensional CT images or MRI (Magnetic Resonance Imaging) images, and the intra-operative images typically are X-ray fluoroscopy images. A three-dimensional pre-operative plan (e.g., such as planning position of a prosthetic implant with respect to the surrounding bony anatomy) may be integrated onto one or several two-dimensional X-ray images to provide the surgeon with images to evaluate a potential surgical outcome.

The present invention also can be used in treating cancer by radio-therapy. Conventional radio-therapy delivery devices include an imaging device (e.g., producing "portal" images), whereas the present invention can be used to project a three-dimensional radio-therapy plan onto two-dimensional images produced by the imaging device, thereby providing the clinician with a mechanism and technique to evaluate the accuracy with which the therapy will be delivered.

The present invention also can be used in brain surgery, in which case the pre-operative images typically may be three-dimensional CT or MRI images, and the intra-operative images typically may be X-ray images. A three-dimensional surgical plan (e.g., such as planning the removal of a tumor of a specified shape and location relatively to the surrounding imaged anatomy) may be integrated onto one or several two-dimensional X-ray images to provide the surgeon with images to evaluate a potential surgical outcome.

The present invention also can be used in craniofacial surgery. In such a case, the pre-operative images typically would be three-dimensional CT or MRI images, and the intra-operative images typically would be X-ray images. A three-dimensional surgical plan typically would involve osteotomies and the relocation of bone fragments to correct some physical deformities. A robotic device would be used to manipulate bone fragments. The three-dimensional plan would be integrated onto one or several two-dimensional X-ray images to provide the surgeon with images to evaluate a potential surgical outcome, and in particular to compare the resulting images with X-ray images of normal individuals, or to evaluate that the execution of the plan will be correct.

What is claimed is:

1. A system for generating simulated data, comprising:
   a medical imaging camera for generating images;
   a registration device for registering data to a physical space, and to said medical imaging camera; and
   a fusion mechanism for fusing said data and said images to generate simulated data,
   wherein said simulated data comprises multiple alternative post-operative conditions.

2. The system according to claim 1, wherein said data comprises pre-operative images and said images comprise intra-operative images.

3. The system as in claim 2, wherein the pre-operative data comprises data of a surgical plan including a position of a component, and a three-dimensional shape of said component.

4. The system as in claim 3, wherein said component comprises an implant for a patient.

5. The system according to claim 1, wherein said data comprises a two-dimensional image.

6. The system according to claim 1, wherein said simulated data comprises simulated post-operative images.

7. The system according to claim 1, wherein said fusion mechanism generates said simulated data while a surgery is being performed.

8. The system as in claim 1, wherein said medical imaging camera comprises a two-dimensional (2D) X-ray camera.

9. The system as in claim 1, wherein said fusion mechanism comprises a data processor.

10. The system according to claim 1, wherein said fusion mechanism fuses said data with said images by integrating a two-dimensional projection of a silhouette of a three-dimensional implant model in an X-ray image.

11. The system according to claim 10, wherein said fusion mechanism uses a calibration of the X-ray image, to determine a center of perspective whose location represents an estimate of a location of an X-ray source,
   said center of perspective being used to compute silhouette curves on the three-dimensional implant model.

12. The system according to claim 11, wherein said silhouette curves are such that rays emanating from the center of perspective and tangent to the three-dimensional model meet the three-dimensional implant model on a silhouette curve.

13. The system according to claim 1, wherein said simulated data are formed by fusing intra-operative images with registered pre-operative data.

14. A system for generating simulated data, comprising:
a medical imaging camera for generating images;
a registration device for registering data to a physical space, and to said medical imaging camera;
a fusion mechanism for fusing said data and said images to generate simulated data; and
another medical imaging camera for collecting said data, wherein said medical imaging camera collects said images.

15. The system as in claim 14, wherein said another imaging camera comprises an X-ray, computed tomography (CT) scanner.

16. A system for generating simulated post-operative data, comprising:
an imaging camera;
a registration device for registering data to a physical space, and to the imaging camera; and
a fusion mechanism for fusing said data and intra-operative images to generate simulated data,
wherein said simulated data comprises multiple alternative post-operative conditions.

17. The system according to claim 16, wherein data comprises pre-operative images and other pre-operative data, and wherein said simulated data comprises simulated post-operative images.

18. The system as in claim 17, wherein the pre-operative data comprises data of a surgical plan including a position of a component, and a three-dimensional shape of said component.

19. The system as in claim 18, wherein said component comprises an implant for a patient.

20. The system according to claim 16, wherein said fusion mechanism generates said simulated data while a surgery is being performed.

21. The system as in claim 16, wherein said imaging camera comprises a two-dimensional (2D) X-ray camera.

22. The system as in claim 16, wherein said fusion mechanism comprises a data processor.

23. A system for generating simulated post-operative data, comprising:
an imaging camera;
a registration device for registering data to a physical space, and to the imaging camera;
a fusion mechanism for fusing said data and intra-operative images to generate simulated data;
a calibration mechanism for calibrating said imaging camera; and
another imaging camera for collecting said pre-operative images, wherein said imaging camera collects said intra-operative images,
wherein data comprises pre-operative images and other pre-operative data, and wherein said simulated data comprises simulated post-operative images.

24. The system as in claim 23, wherein said another imaging camera comprises an X-ray, computed tomography (CT) scanner.

25. A system for providing intra-operative visual evaluations of potential surgical outcomes, using medical images, comprising:
a first medical imaging camera for collecting pre-operative images;
a second medical imaging camera for collecting intra-operative images, while a surgery is being performed;
a registration mechanism for registering said pre-operative images and other pre-operative data to a physical space, and to said second medical imaging camera; and
a fusion mechanism for fusing said pre-operative data and said intra-operative images to generate simulated post-operative images.

26. A system for providing advice to a surgeon without requiring physical manipulation of objects inside and in a vicinity of a patient, said system comprising:
a manipulation device for manipulating one or a plurality of virtual objects;
a registration mechanism for registering the one or plurality of virtual objects to a physical space, and to an imaging camera; and
a fusion mechanism for fusing the one or plurality of virtual objects with an inter-operative image,
wherein said fusion mechanism generates images representing multiple simulated alternative post-operative conditions.

27. A robotically-assisted surgical system, comprising:
a surgical robot;
a first medical imaging camera for collecting pre-operative data;
a second medical imaging camera for collecting intra-operative images;
a registration mechanism for registering said pre-operative data to the surgical robot, and to the second medical imaging camera; and
a fusion mechanism for fusing said pre-operative data and said intra-operative images to generate simulated data.

28. A system for comparing a plurality of methods for registering pre-operative data with a physical space, comprising:
a first medical imaging device for collecting pre-operative data;
a second medical imaging device for collecting intra-operative images;
an image registration mechanism for registering the second medical imaging device to a physical space;
a plurality of pre-operative-data-to-physical-space registration mechanisms for registering said pre-operative data to the physical space; and
a fusion mechanism for fusing said pre-operative data, that are registered using the plurality pre-operative-data-to-physical-space registration mechanisms, and said intra-operative images, to generate new images.

29. A system for assisting a surgeon in a registration of pre-operative data with a physical space, comprising:
means for collecting pre-operative data;
means for collecting intra-operative images;
an image registration mechanism for registering the intra-operative image collecting means to a physical space;
a plurality of pre-operative-data-to-physical-space registration mechanisms for registering said pre-operative data to the physical space;
a fusion mechanism for fusing said pre-operative data, that are registered using the plurality of pre-operative-data-to-physical-space registration mechanisms, and said intra-operative images, to generate new images; and
a constraint mechanism for specifying positional constraints on a three-dimensional position of a physical object that is moved during surgery,
wherein said new images comprise images representing multiple alternative post-operative conditions.

30. A system for assisting a surgeon in a registration of pre-operative data with a physical space, comprising:

means for collecting pre-operative data;
means for collecting intra-operative images;
an image registration mechanism for registering the intra-operative image collecting means to a physical space;
a plurality of pre-operative-data-to-physical-space registration mechanisms for registering said pre-operative data to the physical space;
a fusion mechanism for fusing said pre-operative data, that are registered using the plurality of pre-operative-data-to-physical-space registration mechanisms, and said intra-operative images, to generate new images;
a constraint mechanism for specifying positional constraints on a three-dimensional position of a physical object that is moved during surgery; and
a refinement mechanism for refining a surgical plan by refining the constraints on the three-dimensional position of a physical object that is moved during surgery.

31. A robotically-assisted surgical system, comprising:
a surgical robot;
an image registration mechanism for registering a medical imaging camera to a physical space;
a plurality of pre-operative-data-to-physical-space registration mechanisms for registering pre-operative data to the physical space;
a fusion mechanism for fusing said pre-operative data, that are registered using the plurality of pre-operative-data-to-physical-space registration mechanisms, and intra-operative images produced by said imaging camera, to generate new images; and
a refinement mechanism for refining a surgical plan by refining constraints on a three-dimensional position of a physical object that is moved during surgery,
wherein said new images comprise images representing multiple alternative post-operative conditions.

32. The system according to claim 31, further comprising:
a constraint mechanism for specifying positional constraints on the three-dimensional position of the physical object that is moved during surgery.

33. The system according to claim 31, wherein said surgical robot includes an internal calibration system, said system further comprising:
a graphical warning mechanism for providing a visual representation of an outcome of a surgical plan, and potential failure of the surgical plan resulting from the internal failure of the calibration system of said robot.

34. A system for assessing accuracy of a proposed execution of a pre-operative surgical plan, comprising:
an image device for obtaining intra-operative images of an anatomical feature of interest; and
a data processor for computing a projection of a pre-operative three-dimensional model of an implant or planned trajectory onto the intra-operative image,
wherein said intra-operative image comprises an image representing multiple alternative post-operative conditions.

35. The system according to claim 34, further comprising a display system for displaying an output of said data processor while a surgery is on-going.

36. A method of generating simulated data, comprising:
registering data to a physical space, and to a medical imaging camera; and
fusing said data and said images to generate simulated data,
wherein said simulated data comprises multiple alternative post-operative conditions.

37. A method of generating simulated post-operative data, comprising:
collecting pre-operative data and collecting intra-operative images;
registering said pre-operative data to a physical space, and to a medical imaging camera; and
fusing said pre-operative data and said intra-operative images to generate simulated post-operative data,
wherein said simulated post-operative data comprises multiple alternative post-operative conditions.

38. A method of generating simulated post-operative data, comprising:
collecting pre-operative data and collecting intra-operative images;
registering said pre-operative data to a physical space, and to a medical imaging camera;
fusing said pre-operative data and said intra-operative images to generate simulated post-operative data; and
calibrating the medical imaging camera,
wherein the pre-operative data comprises data of a surgical plan including a position of a component, and a three-dimensional shape of said component.

39. The method of claim 38, wherein said component of said surgical plan includes an implant position.

40. A signal-bearing medium tangibly embodying a program of machine-readable instructions executable by a digital processing apparatus to perform a method for computer-implemented generating of simulated data, comprising:
registering data to a physical space, and to a medical imaging camera; and
fusing said data and said images to generate simulated data,
wherein said simulated data comprises multiple alternative post-operative conditions.

41. A signal-bearing medium tangibly embodying a program of machine-readable instructions executable by a digital processing apparatus to perform a method for computer-implemented generating simulated post-operative data, comprising:
collecting pre-operative data and collecting intra-operative images;
registering said pre-operative data to a physical space, and to a medical imaging camera; and
fusing said pre-operative data and said intra-operative images to generate simulated post-operative data,
wherein said simulated post-operative data comprises multiple alternative post-operative conditions.

42. A system for generating simulated data, comprising:
a medical imaging camera for generating images;
a registration device for registering data to a physical space, and to said medical imaging camera; and
a fusion mechanism for fusing said data and said images to generate simulated data,
wherein said fusion mechanism fuses by projecting a silhouette curve of said data by considering in turn each new pixel, determining a line in three-dimensions corresponding to that pixel by image calibration, computing a distance from a line to the simhouette curve, and assigning a pixel gray-scale value depending on the distance.

43. The system according to claim 42, wherein said fusion mechanism assigns pixel gray-scale values corresponding to a distance, wherein if the distance is less than a first predetermined value, then the gray-scale value is set to a first predetermined number.

44. The system according to claim 43, wherein if the distance is less than a second predetermined value, then the gray-scale value is set to a second predetermined number larger than said first predetermined number.

45. The system according to claim 44, wherein if the distance is less than a third predetermined value greater than said first and second predetermined values, then the gray-scale value is set to a third predetermined number larger than said first and second predetermined numbers.

46. The system according to claim 45, wherein if the distance is greater than or equal to said third predetermined value, then the gray-scale value is not modified for projecting the silhouette curves.

* * * * *